United States Patent [19]

Wang

[11] Patent Number: 5,011,943
[45] Date of Patent: Apr. 30, 1991

[54] FK-506 $C_{10}$-$C_{24}$ PROCESS INTERMEDIATES

[75] Inventor: Zhaoyin Wang, Pierrefonds, Canada

[73] Assignee: Merck Frosst Canada, Inc., Kirkland, Canada

[21] Appl. No.: 399,206

[22] Filed: Aug. 28, 1989

[51] Int. Cl.$^5$ .................. C07D 309/30; C07D 319/06; C07C 69/767; C07C 43/15

[52] U.S. Cl. .................................. 549/214; 549/292; 549/369; 549/374; 556/444; 556/482; 556/485; 560/111; 560/112; 560/262; 568/660; 568/662; 568/673; 568/675

[58] Field of Search ............... 549/214, 292, 369, 374; 560/111, 112, 262; 568/654, 673, 675, 660, 662; 556/482, 444, 485

[56] References Cited

FOREIGN PATENT DOCUMENTS 0184162 11/1985 European Pat. Off. .

OTHER PUBLICATIONS

Askin et al., Tet. Letters, 29: 277–280 (1988).
Askin et al., Tet. Letters, 29: 4245–4248 (1988).
Askin et al., Tet. Letters 30: 671–674 (1989).
Dess & Martin, J. Org. Chem., 48: 4155–4156 (1983).
Egbertson & Danishefsky, J. Org. Chem., 54: 11–12 (1989).
Evans et al., J. Am. Chem. Soc., 103: 2127–2129 (1981).
Ireland et al., J. Am. Chem. Soc., 98: 2868–2877 (1976).
Ireland and Wipf, Tet. Letters, 30: 919–922 (1989).
Jones, A. B. et al., J. Org. Chem., 54, 17–19 (1989).
Jones, T. K. et al., J. Am. Chem. Soc., 111: 1157–1159 (1989).
Kocienski et al., Tet. Letters, 29, 4481–4484 (1988).
Martin et al., J. Am. Chem. Soc., 103: 6237–6240 (1981).
Mills et al., Tet. Letters, 29: 281–284 (1988).
Neeman & Hashimoto, J. Am. Chem. Soc., 84: 2972–2978 (1962).
Oikawa et al., Tet. Letters, 24: 4037–4040 (1983).
Prasit & Rokach, J. Org. Chem., 53: 4421–4422 (1988).
Schreiber & Smith, J. Org. Chem., 54: 9–10 (1989).
Tanaka et al., J. Am. Chem. Soc., 109: 5031–5033 (1987).
Smith & Hale, Tet. Letters, 30: 1037–1040 (1989).
Villalobos & Danishefsky, J. Org. Chem., 54: 12 (1989).
Williams & Benbow, J. Org. Chem., 53: 4643–4644 (1988).

Primary Examiner—Mukund J. Shah
Assistant Examiner—Philip Datlow
Attorney, Agent, or Firm—Joseph F. DiPrima; William H. Nicholson

[57] ABSTRACT

A process is described for the improved synthesis of the optically pure $C_{10}$-$C_{24}$ fragment of the macrolide structure of the immunosuppressant FK-506. This compound is also useful as an intermediate for preparing FK-506 derivatives.

10 Claims, No Drawings

FK-506 $C_{10}$–$C_{24}$ PROCESS INTERMEDIATES

BACKGROUND OF THE INVENTION

This invention relates to a process for producing the optically pure $C_{10}$–$C_{24}$ fragment of FK-506 useful as an intermediate in synthesizing the FK-506 immunosuppressant and derivatives thereof.

The novel 23-membered tricyclomacrolide FK-506 recently isolated and characterized by Tanaka, Kuroda and co-workers (J. Am. Chem. Soc. 109, 5031 (1987) and EPO Publication No. 0184162) has been shown to possess exceptional immunosuppressive activity. The potential usefulness of such an agent in bone narrow and organ transplantations coupled with its unique structural features has prompted many in the field to initiate an effort towards the total synthesis of FK-506.

A highly stereoselective general synthesis of a protected $C_{10}$–$C_{18}$ subunit, in its correct absolute configuration, has been achieved as reported by D. Askin, R. P. Volante, R. A. Reamer, K. M. Ryan and I. Shinkai in Tetrahedron Letters 29, 277, 281 and 4245 (1988), hereby incoporated by reference. See also: (a) Villalobos, A; Danishefsky, S. J., J. Org. Chem., 54, 12(1989); (b) Schreiber, S. L.; Smith, D. B., Ibid, 54 9(1989); (c) Egbertson, M.; Damishefsky, S. J., Ibid, 54, 11(1989); (d) Scheiber, S. L.; Sammakia, T.; Uehling, D. E., Ibid, 54, 16(1989).

A highly selective general synthesis of a protected $C_{10}$–$C_{23}$ subunit of FK-506, in its correct absolute configuration has been achieved as reported by A. B. Smith III and K. J. Hale (Tetrahedron Letters 30, 1037(1989)). That process has the disadvantages of poor stereoselectivity at the $C_{11}$ center (fractional crystallization is required to separate the stereoisomers) and substituents at the $C_{10}$ and $C_{21}$ centers which do not correspond to the natural product. Furthermore, those substituents can not be readily converted to the substituents of the natural product.

What is needed is an overall general synthesis utilizing readily available starting materials which would allow the synthesis of the $C_{10}$–$C_{24}$ fragment of FK-506 incorporating the naturally occurring substituents and also allow for other substituents to be incorporated. Such fragments may be utilized in a convergent total synthesis of FK-506 and related macrolides, the latter which may exhibit greater immunosuppressant acitivity then the naturally occurring form itself.

SUMMARY OF THE INVENTION

We have discovered a method for providing the optically pure $C_{10}$–$C_{24}$ FK-506 fragment. The simplified process for this general sequence is illustrated in following Flow Sheet A.

As seen, the method involves the preparation of the important precursor, 28, to the immunoregulant FK-506 (see Flow Sheet B). The availability of compound 28 by this procedure will enable the synthesis of medicinally active analogs of FK-506.

By this invention, there is provided a process comprising the steps of:

(a) Contacting 1 with propionic anhydride in the presence of an organic base in an inert solvent and at a temperature in the range from 0° to 50° C. for a sufficient time to form the O-acyl derivative I.

(b) Contacting I with a strong organic base and excess silylating agent in inert solvent and a temperature in the range from −100° C. to 0° C. for a sufficient time for the Ireland-Claisen rearrangement to occur and then contacting the product of that reaction in situ with a reducing agent to provide the alcohol II.

(c) Contacting II with a strong base and a protecting group reagent in an inert solvent and a temperature in the range from 20° C. to 100° C. for a sufficient time for III to form.

(d) Contacting III with an aqueous acid/organic solvent mixture at a temperature in the range from 20° C. to 100° C. for a sufficient time for the hydrolysis product IV to form.

(e) Contacting the diol IV with a silylating agent and a base in inert solvent and a temperature in the range from 0° C. to 50° for a sufficient time for the primary siloxy V to form.

(f) Submitting V to Sharpless epoxidation conditions in inert solvent and temperature in the range from −78° C. to 0° C. for sufficient time to form the epoxide VI.

(g) Contacting VI with an alkylating agent and a strong base in inert solvent and a temperature in the range from −20° C. to 20° C. for a sufficient time to form the ether VII.

(h) Contacting VII with tetrabutyl ammonium fluoride in inert solvent and a temperature in the range from 0° C. to 50° C. for a sufficient time for desilylation to occur to provide VIII.

(i) Contacting VIII with an oxidizing agent in inert solvent and a temperature in the range from 0° C. to 50° C. for a sufficient time to form the aldehyde IX.

(j) Contacting IX with an organophosphorane in inert solvent and a temperature in the range from 0° C. to 70° C. for a sufficient time to form the unsaturated ester X.

(k) Contacting X with hydrogen gas and a catalytic metal in inert solvent and a temperature in the range from 0° C. to 30° C. for a sufficient time to completely reduce the double bond to provide XI.

(l) Contacting XI with excess alkali in alcohol and a temperature range from 20° C. to 110° C. for a sufficient time to cleave the epoxide, then contacting the product from that reaction with catalytic acid in inert solvent and a temperature in the range from 0° C. to 50° C. for a sufficient time to form the lactone XII.

(m) Contacting XII with an alkylating agent in inert solvent and a temperature range from −20° C. to 20° C. for a sufficient time to form the triether XIII.

(n) Contacting 15 with dibutylboron triflate and diisopropylethylamine in inert solvent and a temperature in the range from −100° C. to 0° C. for a sufficient time to form the boron enolate, which is then contacted in situ with a benzyl protected oxypropionaldehyde in the same solvent and temperature for a sufficient time to form the alcohol XIV.

(o) Contacting XIV with a trialkyl halo silane, benzyl halide or alkanoyl halide in the presence of an organic amine base or, if the hydroxy protecting group P1 is a benzyl group, contacting XIV with 4,5-dichloro-1,4-cyclohexadiene-1,2-dicarbonitrile (DDQ), in inert solvent and a temperature range from 0° to 50° C. for a sufficient time to form the bisprotected compound XV.

(p) Contacting XV with lithium hydroxide and hydrogen peroxide in aqueous tetrahydrofuran and a temperature in the range from −20° C. to 20° C. for a sufficient time to form the acid XVI.

(q) Contacting XVI with lithium aluminum hydride in inert solvent and a temperature in the range from −20° C. to 20° C. for a sufficient time to form the alcohol XVII.

(r) Contacting XVII with oxalyl chloride, dimethylsulfoxide, and triethylamine in inert solvent and a temperature range from −100° C. to 0° C. for a sufficient time to form the aldehyde XVIII.

(s) Contacting XVIII with (carbethoxyethylidene)triphenylphosphorane in inert solvent and a temperature range from 50° C. to 150° C. for a sufficient time to form the unsaturated ester XIX.

(t) Contacting XIX with lithium aluminum hydride in inert solvent and a temperature range from −30° C. to 20° C. for a sufficient time to form the alcohol XX.

(u) Contacting XX with carbon tetrabromide and triphenylphosphine in inert solvent and a temperature range from −20° C. to 20° C. for a sufficient time to form the bromide XXI.

(v) Contacting XXI with sodium iodide in inert solvent and a temperature range from 20° to 100° C. for a sufficient time to form the iodide XXII.

(w) Contacting XIII with sodium hexamethyldisilazide in inert solvent and a temperature range from −78° C. to −20° C. for a sufficient time to form the enolate and contacting this solution with XXII for a sufficient time to form XXIII.

(x) Contacting XXIII with lithium aluminum hydride in inert solvent and a temperature range from −20° C. to 20° C. for a sufficient time to form the diol XXIV.

(y) Contacting XXIV with p-toluenesulfonyl chloride, triethylamine and catalytic 4-dimethylamino pyridine in inert solvent and a temperature range from 0° to 40° C. for a sufficient time to form the tosylate XXV.

(z) Contacting XXV with a protecting group reagent and a base in invert solvent and temperature range from −10° to 30° C. for a sufficient time to form the protected alcohol XXVI.

(aa) Contacting XXVI with lithium triethylborohydride in inert solvent and a temperature range of 0° to 30° C. for a sufficient time to form XXVII.

FLOW SHEET A

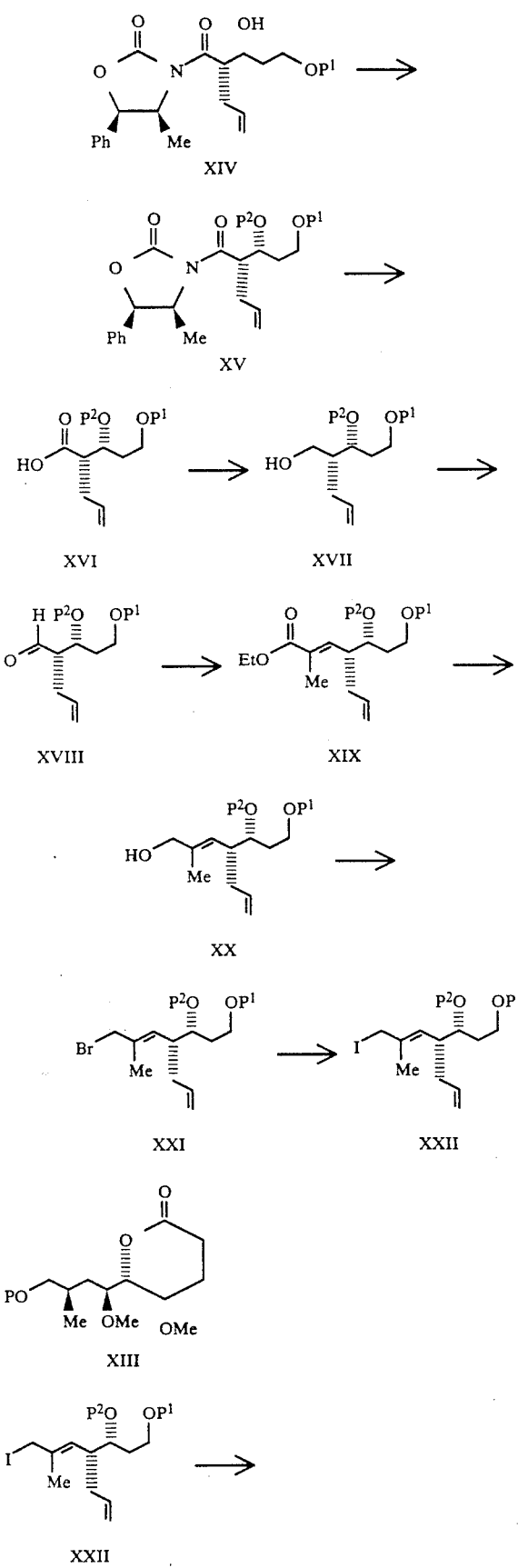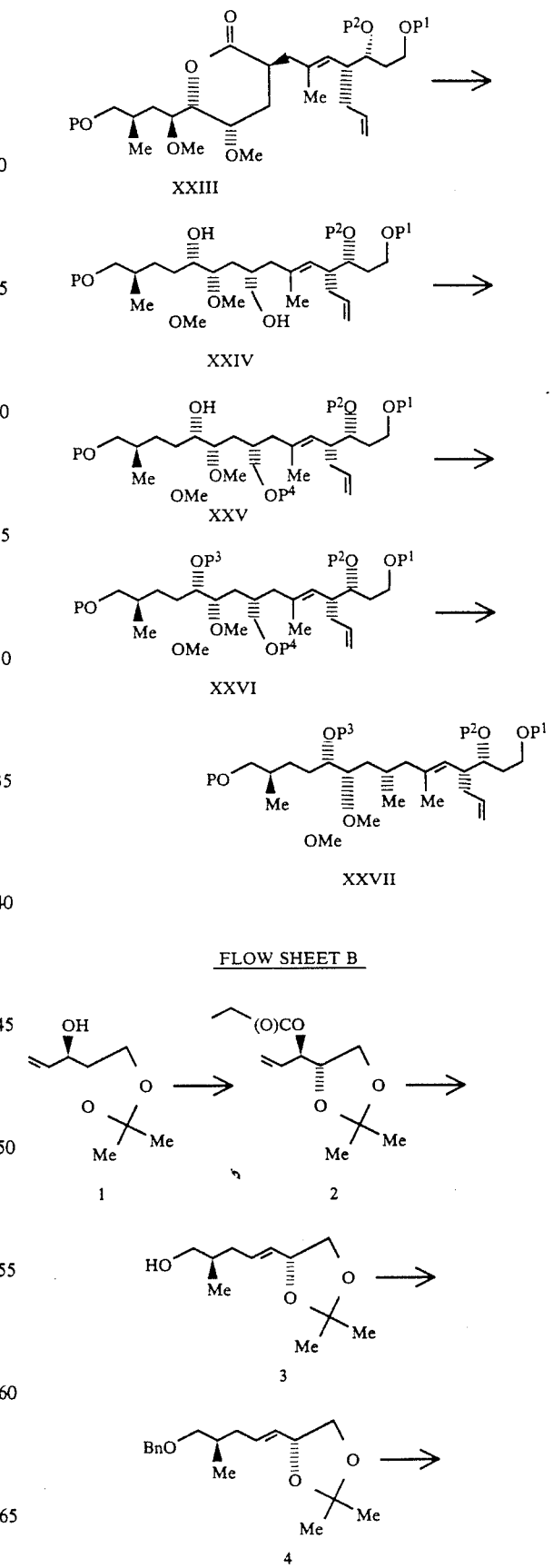

-continued
FLOW SHEET B
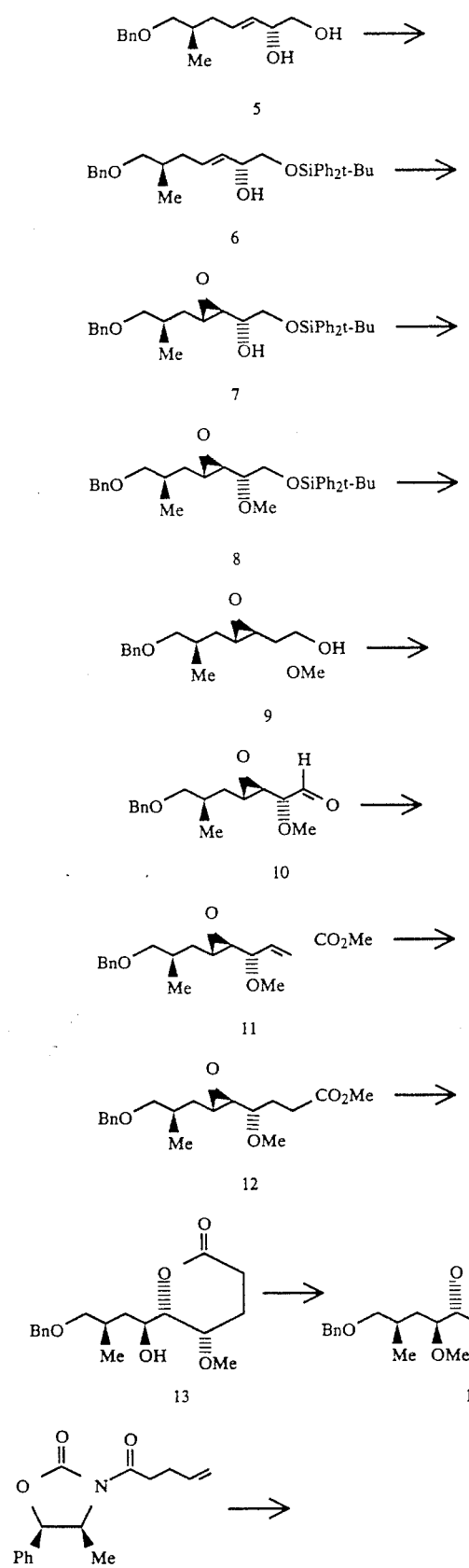
-continued
FLOW SHEET B
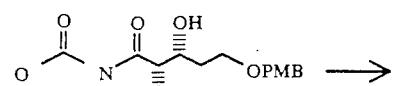
16
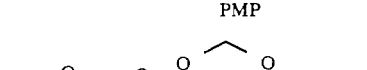
17
18
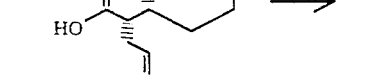
19  20
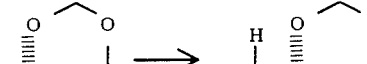
21
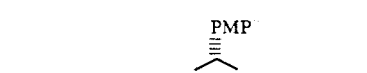
22  23
14

-continued
FLOW SHEET B

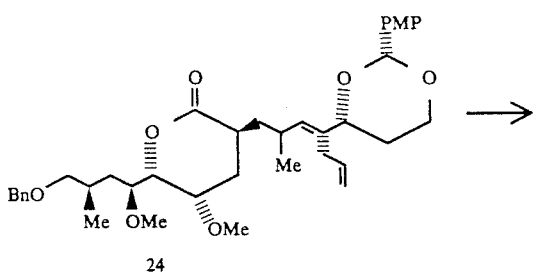

24

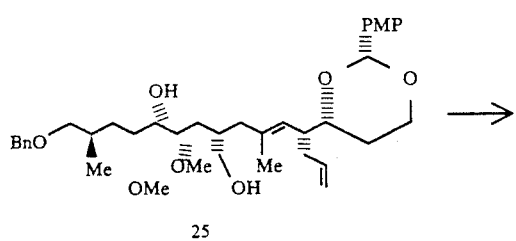

25

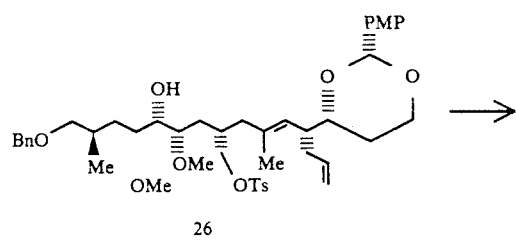

26

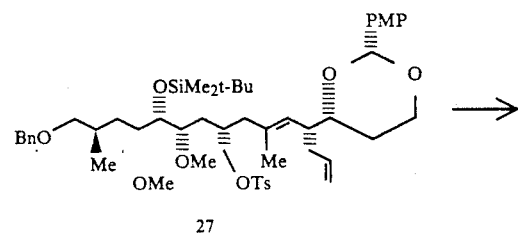

27

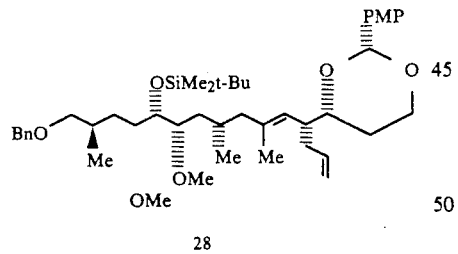

28

Further provided is a compound of the formula:

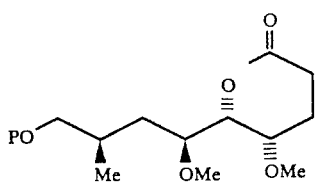

XIII where P is a hydroxy protecting group.
Also provided is a compound of the formula:

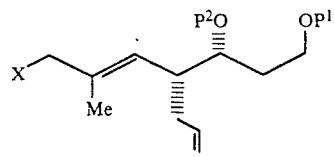

XXII where X is a halide and $P^1$ and $P^2$ are hydroxy protecting groups which may be different or the same or $P^1$ and $P^2$ may be combined to form a aromatic methine diradical.

Furthermore, there is provided a compound of the formula:

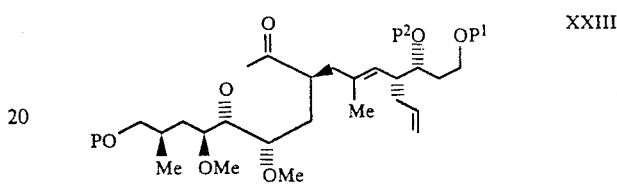

XXIII where P, $P^1$ and $P^2$ are hydroxy protecting groups as described above.

Also provided is a compound of the formula:

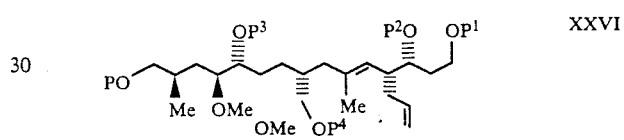

XXVI where P, $P^1$, $P^2$, $P^3$ and $P^4$ are independently hydroxy protecting groups, as described above, or hydrogen, with the proviso that $P^3$ and $P^4$ are different.

In addition, there is provided a compound of the formula:

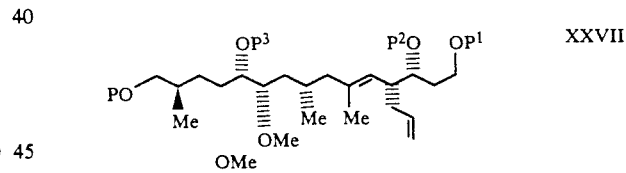

XXVII where P, $P^1$, $P^2$ and $P^4$ are independently hydroxy protecting groups as described above.

BRIEF DESCRIPTION OF THE INVENTION AND THE PREFERRED EMBODIMENTS

The invention can be readily understood by referring to the general synthesis scheme in Flow Sheet A.

The starting materials 1 and 15 are known in the art and can be readily prepared in large quantities from readily available starting materials, e.g. L-arabinose, and methylphenyloxazolidenone and 4-pentenoic acid respectively, using chemistry known in the art.

The hydroxy protecting groups described herein are conventional, as illustrated by P, and the class of hydroxy protecting groups includes trisubstituted silyl, benzyl, and substituted benzyl, and aroyl and alkanoyl. Hydroxy protecting groups, their structure, formation, removal and utility, are described in "Protective Groups in Organic Synthesis" by Theodora W. Greene, published by John Wiley, 1981, New York, Chapter 2, pages 10-87, titles Protection for the Hydroxyl Group, including 1,2— and 1,3-diols, hereby incorporated by reference.

Representative trisubstituted silyl groups, removable by acidic or fluoride hydrolysis are: trimethylsilyl, triethylsilyl, isopropyldimethylsilyl, t-butyldimethylsilyl (TBS), (triphenylmethyl)dimethylsilyl, t-butyldiphenylsilyl, methyldiisopropylsilyl, methyldi-t-butylsilyl, tribenzylsilyl, tri-p-xylylsilyl, triisopropylsilyl, triphenylsilyl, and the like, preferably t-butyldimethylsilyl.

Representative benzyl groups removed by catalytic hydrogenation or dissolving metal conditions, e.g. $Li/NH_3$ include: benzyl, (Bn), 3,4-dimethoxybenzyl, p-methoxybenzyl (PMB), m-nitrobenzyl, p-nitrobenzyl, p-bromobenzyl, p-chlorobenzyl, p-cyanobenzyl, and the like, preferably benzyl and p-methoxybenzyl.

Representative $C_1$–$C_{10}$ alkanoyl and aroyl protecting groups removable by basic hydrolysis or hydride reduction are: pivaloyl, isobutroyl, adamantoyl, benzoyl, and the like, preferably pivaloyl.

The term "substituted phenyl group" may include phenyl, nitrophenyl, methoxyphenyl, chlorophenyl and the like. Attachment to the molecule may be at the para, ortho or meta position.

The term "halide" refers to iodide, chloride or bromide.

The term "aromatic methine diradical" may include phenylmethine, p-methoxyphenlmethine, p-nitrophenylmethine and the like. Preferably $P^1$ and $P^2$ are combined to form p-methoxyphenylmethine.

The first step of the synthesis, referring to Flow Sheet A, is the synthesis of the ester I, accomplished by the propionation of alcohol 1.

1 is treated with a solution of an organic nitrogen base, propionic anhydride, and, optionally, a catalytic amount of a different organic nitrogen base.

The organic nitrogen base functions as a hydrogen acceptor and can be a tertiary amine including trimethylamine, triethylamine, tri-n-butylamine, diisopropylethylamine, lutidine, 4-(dimethylamino)pyridine, imidazole and the like, preferably triethylamine. Preferably a second base is employed in a catalytic amount. This second base is preferably 4-(dimethylamino)pyridine.

The molar ratios of 1 organic base:propionic anhydride:catalytic different organic nitrogen base is generally in the range of 1:2:1.2:0.05.

The inert solvent used can be a $C_1$–$C_4$ halogenated alkane, e.g. dichloromethane; an aromatic hydrocarbon, e.g. benzene, toluene, xylene, a $C_2$–$C_4$ linear or cyclic ether, e.g. diethylether, tetrahydrofuran (THF) or other aprotic polar solvents, e.g. dimethylformamide, acetone, and the like, and preferably methylene chloride.

The temperature of the propionation is in the range of 0° to 50° C.

Conventional workup of the reaction yields I.

Conversion of I to the unsaturated alcohol II involves an Ireland Claisen rearrangement followed by reduction of the acid product and is illustrated in Flow Sheet A. I is treated with a strong alkali ammonium base and a trialkylhalosilane in the first part of the reaction. The solution containing the intermediate is then treated with a reducing agent and an organic nitrogen base.

The strong alkali ammonium base may be purchased commercially in solution or may be formed immediately before use, and functions as a proton abstractor. This base may be formed by the reaction of an organic metal including n-butyl lithium, t-butyl lithium and the like; with a secondary amine, including diisopropylamine, dicyclohexlamine, isopropylcyclohexylamine, bis(-trimethylsilyl)amine, and the like. Preferably such a strong alkali ammonium base is formed from the reaction of n-butyl lithium and diisopropylamine.

The trialkylhalosilane can be trimethyl chlorosilane, triethylchlorosilane, t-butyldimethylchlorosilane and the like.

The reducing agent employed in the second part of the reaction to form II may be diborane, sodium borohydride, lithium aluminum hudride and the like. Preferably the reducing reagent is lithium aluminum hydride.

The reaction is conducted in an inert solvent of the same class as described above for the preparation of I. Preferred is tetrahydrofuran.

The organic nitrogen base employed in the second part of the reaction is of the same class as described above for the preparation of I. Preferably the organic nitrogen base is triethylamine.

The conversion of II to III involves replacement of the alcoholic proton with a hydroxy protecting group as described herein (see Flow Sheet A). This is generally accomplished by contacting a trialkyl halo silane, benzyl halide or alkanoyl halide and the like, preferably benzyl bromide corresponding to the protecting group to a salt of II, e.g. sodium salt in an inert solvent, at a temperature of about 0°–25°, for a sufficient time to effect a complete reaction. A catalyst may be employed in this formation of a salt of II may be accomplished by treating II with a alkali hydride in an inert solvent of the same class as described above. The alkali hydride may be sodium hydride, cesium hydride, lithium hydride and the like. Preferably sodium hydride is employed.

The trialklyl halo silane is of the same class as described above for the conversion of I to II.

The benzyl halide may be benzyl bromide, benzyl chloride, benzyl iodide, p-methoxybenzyl bromide and the like.

The alkanoyl halide may be acetyl chloride, pivaloyl chloride, benzoyl chloride and the like.

The catalyst that may be employed in the conversion may be a tetraalkylammonium salt, such as tetraethylammonium iodide, tetrabutylammonium iodide and the like. Preferably tetrabutylammonium iodide is employed.

The reaction is conducted in an inert solvent of the same class as described above for the preparation of I. Preferred is tetrahydrofuran.

The conversion of III to IV involves hydrolysis of the acetonide group to provide a diol (see Flow Sheet A). This is generally accomplished by reacting III with an aqueous acid in inert organic solvent at a temperature of about 50°–100° C. for a sufficient time to effect hydrolysis.

The aqueous acid can be 2N aqueous hydrochloric acid solution, glacial acetic acid/water mixture, dilute aqueous sulfuric acid solution and the like. Preferably the aqueous acid is a 4:1 v/v glacial acetic acid/water mixture.

The reaction is conducted in an inert solvent of the same class as described herein above for the preparation of I. Preferred is tetrahydrofuran.

The conversion of IV to V involves selective replacement of the primary alcoholic proton with a hydroxy protecting group which is different then the hydroxy protecting group already present on IV (see Flow Sheet A). This is generally accomplished by contacting a silyl halide, benzyl halide, alkanoyl halide and the like, corresponding to the protecting group with IV in the presence of an organic nitrogen base in an inert solvent at a temperature of about 0° to 25° C., for a sufficient time to effect complete replacement of the proton.

Preferably a silyl halide which is of the same class as described herein above for the preparation of III is contacted with IV. Preferably tert-butyldiisopropylchlorosilane is employed.

The organic nitrogen base functions as a proton scavenger and is of the same class as described above for the preparation of I. Preferably the base is imidazole.

The reaction is conducted in an inert solvent of the same class as described above. Preferred is dimethylformamide.

The conversion of V to VI involves stereoselective epoxidation of the double bond of V (see Flow Sheet A). This is generally accomplished by contacting V with tert-butyl hydroperoxide, (+)-diethyltartrate and titanium tetraisopropoxide in an inert solvent at a temperature of about −20° to 0° C. for a sufficient time to completely form the epoxide.

The reaction is conducted in an inert solvent of the same class as described above for the preparation of I. Preferred is methylene chloride.

The conversion of VI to VII involves methylation of the hydroxy group (see Flow Sheet A). This is generally accomplished by adding a methylating agent, e.g. methyl iodide, methyl bromide, and the like, preferably methyl iodide, to a salt of VI e.g. sodium salt in an inert solvent, at a temperature of about 0° to 25° C. for a sufficient time to effect a significant yield of VII.

The formation of the salt of VI may be accomplished by the same procedure as described for formation of the salt of II hereinabove. Preferably sodium hydride is employed.

The reaction is conducted in an inert solvent of the same class as described above for the preparation of I. Preferred is tetrahydrofuran.

The conversion of VII to VIII involves removal of one of the hydroxy protecting groups $P^1$ from VII (see Flow Sheet A). This is generally accomplished by contacting VII with tetrabutylammonium fluoride in an inert solvent at 0° to 30° C. for a sufficient time for complete removal of the hydroxy protecting group.

The reaction is conducted in an inert solvent of the same class as described hereinabove for the preparation of I. Preferred is tetrahydrofuran.

The conversion of VIII to IX involves oxidation of the primary hydroxy to an aldehyde (see Flow Sheet A). This is generally accomplished by contacting VIII with an oxidizing agent in an inert solvent at 0° to 30° C. for a sufficient time for complete oxidation to occur.

The oxidizing agent may be chromic oxide, chromium trioxide/pyridine complex, a chiral periodinane (Dess, D. B., Martin, J. C. J. Org. Chem. 48,4155 (1983)) and the like. Preferably the Dess/Martin periodinane is employed in the presence of an equimolar quantity of tert-butanol.

The inert solvent is of the same class as described above for the formation of I. Preferably methylene chloride is employed.

The conversion of IX to X involves contacting the aldehyde IX with an alkyloxycarbonyl phosphorane in an inert solvent at 0° to 50° C. for a sufficient time for complete formation of the olefin (see Flow Sheet A).

The alkoxy carbonyl phosphorane may be methyl(triphenylphosphoranylidene)acetate, ethyl(triphenylphosphoranylidine)acetate and the like. Preferred is methyl(triphenylphosphoranylidene) acetate.

The inert solvent is of the same class as described above for the formation of I. Preferably tetrahydrofuran is employed.

The conversion of X to XI involves reduction of the olefin to the saturated ester (see Flow Sheet A). This is generally accomplished by contacting the olefin with hydrogen gas at positive pressure in the presense of a metal catalyst in an inert solvent at 0° to 25° C. for a sufficient time that all of the olefin has been reduced.

The pressure of the hydrogen gas may be from slightly over 1 atm pressure (termed "balloon pressure") to 44 psi (pounds per square inch).

The metal catalyst employed may be palladium on carbon, palladium oxide, palladium hydroxide, rhodium alumina, and the like. Preferred is 10% palladium on carbon.

The reaction is conducted in an inert solvent of the same class as described above for the preparation of I. Preferred is ethyl acetate.

The conversion of the ester XI to the lactone XII involved hydrolysis of the ester to the corresponding acid which cyclizes to the lactone in the presense of the catalytic acid (see Flow Sheet A). This is generally accomplished by contacting XI with aqueous alkali base, acidifying the product and contacting that intermediate with a catalytic amount of acid in an inert solvent.

The aqueous alkali base may be aqueous solutions of potassium hydroxide, sodium hydroxide and the like. Preferred is a 5N aqueous solution of sodium hydroxide.

The catalytic acid may be trifluoroacetic acid, camphorsulfonic acid and the like. Preferred is camphorsulfonic acid.

The inert solvent in the second step of this conversion is of the same class as described hereinabove for the formation of I. Preferably methylene chloride is employed.

The conversion of the lactone XII to the lactone triether XIII involves methylation of the hydroxyl group (see Flow Sheet A). This is generally accomplished under neutral conditions by contacting XIII with diazomethane in the presense of a catalytic amount of borontrifluoride ether complex in inert solvent at −20° to 0° C. for a sufficient time that all of the alcohol has been methylated.

The inert solvent is of the same class as described hereinabove for the formation of I. Preferably methylene chloride is employed.

The conversion of 15 to XIV involves the aldol reaction of the boron enolate of 15 with the protected hydroxy propanaldehyde (see Flow Sheet A). This is generally accomplished by contacting 15 with dibutylborontriflate and an organic nitrogen base, then contacting that mixture with the protected aldehyde. The reaction generally occurs in an inert solvent at a temperature of about −78° to 0° C. for the first part of the reaction for a sufficient time to completely form the boronenolate and a temperature of about −78° to 30° C. for the second part of the reaction for a sufficient time to completely form the aldol adduct.

The hydroxy protecting group $P^1$ may be trialkylsilyl, alkanoyl, p-nitrobenzyl, p-methoxybenzyl, benzyl and the like. In this reaction, p-methoxybenzyl is preferred.

The organic nitrogen base is of the same class as described for the preparation of I. Preferably the organic nitrogen base is diisopropylethylamine.

The reaction is conducted in an inert solvent of the same class as described hereinabove for the preparation of I. Preferred in methylene chloride.

The conversion of XIV to XV involves replacement of the alcoholic proton with a hydroxy protecting group (see Flow Sheet A). This is generally accomplished by contacting XIV with a trialkyl halo silane, benzylhalide or alkanoyl halide in the presense of an organic nitrogen base in an inert solvent or, if the protecting group $P^1$ is a substituted or unsubstituted benzyl, XIV may be contacted with 2,3-dichloro-5,6-dicyano-1,4-benzoquinone in an inert solvent at a temperature of about 0° to 30° C. for a sufficient time to generate the bisprotected product XV as completely as possible.

The reaction is conducted in an inert solvent of the same class as described above for the preparation of I. Preferred is methylene chloride.

The conversion of XV to XVI involves the hydrogen peroxide catalized cleavage of the oxazolidone group (see Flow Sheet A). This is generally accomplished by contacting XV with an excess of hydrogen peroxide and an alkali hydroxide in an aqueous organic solvent at a temperature of about 0° to 20° C. for a sufficient time to cleave the oxazolidone group completely, then the unreacted hydrogen peroxide is reduced with aqueous sodium sulfite and then acidification of the reaction with an acid.

The alkali hydroxide may be sodium hydroxide, potassium hydroxide, lithium hydroxide and the like. Preferred is lithium hydroxide.

The conversion of XVI to XVII involves the reduction of the carboxylic acid group (see Flow Sheet A). This is generally accomplished by contacting XVI with a reducing agent in an inert solvent at a temperature range of −20° to 20° C. for a sufficient time to effect complete reduction to the alcohol.

The reducing agent employed is of the same class as described hereinabove for the conversion of I to II. Preferred is lithium aluminum hydride.

The reaction is conducted in an inert solvent of the same class as described hereinabove for the preparation of I. Preferred is diethylether.

The conversion of XVII to XVIII involves the oxidation of the alcohol group to an aldehyde (see Flow Sheet A). This is generally accomplished by contacting XVII with oxalyl chloride, dimethylsulfoxide and triethylamine in an inert solvent at a temperature of about −78° to 0° C. for a sufficient time to completely convert the alcohol group to an aldehyde.

The inert solvent employed is of the same class as described hereinabove for the preparation of I. Preferred is methylene chloride.

The conversion of XVIII to XIX involves the formation of the unsaturated ester from the aldehyde group (see Flow Sheet A). This is generally accomplished by contacting XVIII with (carbethoxyethylidene)triphenylphosphorane in an inert solvent at a temperature of about 40° to 60° C. for a sufficient time to completely form the olefin bond.

The reaction is conducted in an inert solvent of the same class described hereinabove for the preparation of I. Preferred is methylene chloride.

The conversion of XIX to XX involves the reduction of the ester group to the primary alcohol (see Flow Sheet A). This is generally accomplished by contacting XIX with a reducing agent in an inert solvent at a temperature of about −20° to 0° C. for a sufficient time to effect complete reduction of the ester.

The reducing agent employed is of the same class as described hereinabove for the conversion of I to II. Preferred is lithium aluminum hydride.

The reaction is conducted in an inert solvent of the same class described hereinabove for the preparation of I. Preferred is diethylether.

The conversion of XX to XXII involves the replacement of the hydroxy group with an iodide group (see Flow Sheet A). This is generally accomplished by first contacting XX with an activating agent and an organic nitrogen base in an inert solvent at a temperature of about −10° to 20° C. for the sufficient time to form the activated intermediate. This intermediate is then contacted with a metal iodide in an inert solvent at a temperature of about 30° to 60° C. for a sufficient time to form XXII.

The activating agent employed in the first part of this conversion may be carbontetrabromide and triphenylphosphine combined, mesyl chloride, tosyl chloride, tosyl anhydride and the like.

The first part of this conversion is conducted in an inert solvent of the same class described hereinabove for the preparation of I. Preferred is methylene chloride.

The metal iodide employed in the second part of this conversion may be potassium iodide, cesium iodide, sodium iodide and the like. Preferred is sodium iodide.

The inert solvent employed in the second part of this conversion is of the same class as described hereinabove for the preparation of I. Preferred is acetone.

The synthesis of XXIII involves the coupling of subunits XIII and XXII (see Flow Sheet A). This is generally accomplished by contacting XXII with a strong alkali ammonium base in an inert solvent at a temperature of about −78° to −44° for a sufficient time to mono-deprotonate the lactone ring. This enolate is then contacted with XIII in the same solvent and the same temperature range as the first part of this reaction.

The strong alkali ammonium base may be sodium bis(trimethylsilyl)amide, lithium diisopropylamide, lithium bis(trimethylsilyl)amide and the like. Preferred is sodium bis(trimethylsilyl)amide.

The reaction is conducted in an inert solvent of the same class as described above for the preparation of I. Preferred is tetrahydrofuran.

The conversion of XXIII to XXIV involves reductive cleavage of the lactone ring (see Flow Sheet A). This is generally accomplished by contacting XXIII with a reducing agent in an inert solvent in a temperature range of −50° to 0° for a sufficient time to completely convert XIII to XXIV.

The reducing agent employed is of the same class as described hereinabove for the conversion of I and II. Preferred is lithium aluminum hydride.

The reaction is conducted in an inert solvent of the same class as described hereinabove for the preparation of I. Preparation is tetrahydrofuran.

The conversion of XXIV to XXV involves the replacement of the primary hydroxy group with a labile group, such as mesylate, tosylate and the like (see Flow Sheet A). This is generally accomplished by contacting XXIV with a sufonylating agent and an organic nitrogen base in an inert solvent at a temperature of about 0° to 30° C. for a sufficient time to completely convert XXIV to XXV.

The sulfonylating agent may be methylsulfonyl chloride, p-toluenesulfonyl chloride, p-toluenesulfonic anhydride and the like. Preferred is p-toluensulfonic chloride.

The organic nitrogen base that is employed is of the same class as described hereinabove in the preparation of the ester I. Preferably the base employed is triethylamine and a second base, 4-(dimethylamino)pyridine is also employed.

The inert solvent that is employed is of the same class as described hereinabove for the preparation of I. Preferred is methylene chloride.

The conversion of XXV to XXVI involves replacement of the alcoholic proton with a hydroxy protecting group as described herein (see Flow Sheet A). This is generally accomplished by contacting XXV with a silyl halide, benzyl halide, alkanoyl halide and the like, and an organic nitrogen base in an inert solvent at a temperature of about 0° to 30° for a sufficient time that the proton has been completely replaced by the protecting group.

Preferably a silyl halide which is of the same class as described hereinabove for the preparation of III is employed. Most preferably (t-butyl)dimethylsilyltriflate is employed.

The organic nitrogen base functions as a proton scavenger and is of the same class as described hereinabove for the preparation of I. Preferably the base is 2,6-lutidene.

The reaction is conducted in an inert solvent of the same class as described above. Preferred is methylene chloride.

The conversion of XXVI to XXVII involves the reduction of the labile group (see Flow Sheet A). This is generally accomplished by contacting XXVI with a hydride source in an inert solvent at a temperature of about 0° to 30° C. for a sufficient time that all of the labile group is displaced.

The hydride source may be lithium aluminum hydride, lithium triethylborohydride and the like.

The reaction is conducted in an inert solvent of the same class as described above for the preparation of I. Preferred is tetrahydrofuran.

The following examples are illustrative for the purposes of carrying out the instant invention and should not be construed as being limitations on the scope or spirit of the instant invention. The compound numbers refer to the numbering in Flow Sheet B.

EXAMPLE 1

Pentene 2

A solution of 1-pentene 3,4,5-triol 4,5-acetonide 1, 14 ml of triethylamine, 9 ml of propionic anhydride and 200 mg of 4-(dimethylamino)-pyridine in 200 ml of methylene chloride was stirred at 0° C. for 5 hours. Water (10 ml) was then added and the stirring continued for 30 minutes. Saturated aqueous sodium bicarbonate (200 ml) was added and the mixture extracted 2 times with 300 ml of ethyl ether. The combined organic phases were dried with sodium sulfate, filtered and concentrated under vacuum. Chromatography of the residue over silica gel (3 pentene: 1ethyl ether) provided the title compound.

$[\alpha]_D^{23} = +4.8$ c=2 CHCl$_3$ p.m.r.: (CDCl3) δ:1.18 (t,3H), 1.38 (s,3H), 1.45 (s,3H), 2.42 (q,2H), 3.82 (dd,1H), 4.14 (dd,1H), 4.25 (m, 1H), 5.35 (m,3H), 5.84 ppm (m,1H).

EXAMPLE 2

Heptenol 3

A 2.5M solution of n-butyl lithium in THF (43 ml) was added to a solution of cyclohexylisopropylamine in 150 ml of THF at 0° C. and the resulting solution cooled to −78° C. A solution of 24 ml of chlorotrimethylsilane in 40 ml of THF was added slowly, followed by a solution of 10 g of the pentene 2 in 30 ml of THF. The solution was stirred at −78° C. for 10 minutes, then 40 ml of triethylamine was added and the solution stirred overnight at room temperature (RT) and stirred for 1.5 hour at 60° C. The solution was cooled to −50° C. and 4.4 g of lithium aluminum hydride was added. The mixture was stirred at 0° C. for 3 hours, then 200 ml of ethyl acetate (EtOAc) and 200 ml of saturated aqueous potassium-sodium tartrate were added. The mixture was stirred for 2 hours at RT and the phases separated. The aqueous phase was extracted with 200 ml of EtOAc and the combined organic phases were dried with sodium sulfate (Na$_2$SO$_4$). Concentration under vacuum provided the title compound.

$[\alpha]_D^{23} = -25.2$ c=2 CHCl$_3$

EXAMPLE 3

Benzylheptene ether 4

A solution of 6.9 g of the alcohol 3, 1.68 g of sodium hydride, 300 mg of tetrabutylammonium iodide and 5.95 g of benzyl bromide in 250 ml of THF was stirred for 4 hours at 60° C. At the end of this time 100 ml of saturated aqueous ammonium chloride solution was added and the mixture extracted with 200 ml of EtOAc and the organic phase was dried with sodium sulfate. Concentration under vacuum provided the title compound.

EXAMPLE 4

Heptene diol 5

A solution of the benzyl ether 4, 80 ml of acetic acid and 20 ml of water in 50 ml of THF was stirred at 70° C. overnight. The solution was then concentrated under vacuum and the residue purified by chromatography over silica gel (3 EtOAc: 2 hexanes) to provide the title compound.

$[\alpha]_D^{23} = -10.7$ c=2.0 CHCl$_3$ p.m.r.: (CDCl3) δ:0.91 (d,3H), 1.80–2.30 (m,3H), 3.30 (d,2H), 3.46 (dd,1H), 3.62 (dd,1H), 4.22 (m,1H), 4.50 (s,2H), 5.45 (dd,1H), 5.75 (dt,1H), 7.26–7.39 pm (m,5H).

EXAMPLE 5

Siloxy heptenol 6

A solution of 6 g of the diol 5, 6.5 ml of t-butyldiphenylchlorosilane and 3.4 g of imidazole in 120 ml of dimethylformamide (DMF) was stirred at 0° C. for 2 hours. The mixture was then concentrated under vacuum and the residue was dissolved in 300 ml of 5 hexanes: 1 EtOAc. The solution was washed with 150 ml of water and then 150 ml of saturated aqueous sodium chloride solution (brine). The organic phase was dried over sodium sulfate and concentrated under vacuum to provide the title compound.

$[\alpha]_D^{23} = -6.5$ c=2.0 p.m.r.: (CDCl3) δ0.90 (d,3H), 1.08 (s,9H), 1.85 (m,3H), 2.60 (d,1H), 3.26 (dd,1H), 4.18 (m,1H), 4.46 (s,2H), 5.38 (dd,1H), 5.68 (dt,1H), 7.31–7.46 (m,15H), 7.64–7.70 ppm (m,4H).

EXAMPLE 6

Epoxide 7

A solution of the siloxy heptenol 6, 5 ml of diisopropyl L-tartrate, 20 ml of a 3M t-butyl hydroperoxide in trimethylpentane solution and 6 ml of titanium(V) isopropoxide in 180 ml of methylene chloride was stirred for 6 hours at $-20°$ C. A solution of 10% tartaric acid in water (100 ml) was added and the mixture was stirred for 30 minutes.

Chromatography of the residue over silica gel (6 hexanes: 1 EtOAc) provided the title compound.

$[\alpha]_D^{23} = -8.8$ c=2.0 p.m.r.: (CHCl$_3$) δ1.03 (d,3H), 1.08 (s,9H), 1.42 (m,1H), 1.82 (m,1H), 2.02 (m,1H), 2.41 (d,1H), 2.81 (dd,1H), 3.01 (m,1H), 3.36 (d,2H), 3.34 (m,1H), 3.78 (d,2H), 4.50 (s,2H), 7.29-7.48 (m,11H), 7.65-7.69 ppm (m,4H).

EXAMPLE 7

Methoxy epoxide 8

A mixture of 9.7 g of the epoxide 7, 2.88 g of sodium hydride (50% in oil) and 10 ml of methyl iodide in 200 ml of THF was stirred 1 hour at 0° C. The mixture was then poured into a mixture of 200 ml of saturated aqueous ammonium chloride solution and hexanes/EtOAc and that mixture was extracted with 300 ml 3 hexanes: 1 EtOAc. The organic phase was dried over sodium sulfate and concentration under vacuum provided the title compound.

$[\alpha]_D^{23} = -10.9$ c=2.0 CHCl$_3$

EXAMPLE 8

Heptenol oxide 9

A solution of the methoxy epoxide 8 and 70 ml of a 1M tetrabutylammonium fluoride in THF solution in 20 ml THF was stirred at RT for 1 hour. The solution was then poured into water and this aqueous solution was extracted 3× with 150 ml of 1 hexane: 1 EtOAc. The organic phases were dried with sodium sulfate and concentrated under vacuum to provide the title compound.

$[\alpha]_D^{23} = -42.7$ c=2.0 p.m.r.: (CHCl$_3$) δ1.03 (d,3H), 1.40 (m,2H), 1.83 (m,1H), 2.05 (m,2H), 2.71 (dd,1H), 3.02 (m,1H), 3.11 (m,1H), 3.34 (dd,1H), 3.40 (dd,1H), 3.43 (s,3H), 3.62 (m,1H), 3.80 (m,1H), 4.52 (s,2H), 7.28-7.36 ppm (m,5H).

EXAMPLE 9

Aldehyde 10

To a solution of 1.03 g of the Dess-Martin periodinane in 10 ml of methylene chloride was added 0.235 ml of t-butanol, then 500 mg of the heptenol oxide 9 was added. The solution was stirred at RT for 1 hour, then 30 ml of ethyl ether was added and the mixture filtered thru silica gel. The filtrate was then concentrated under vacuum to provide the title compound.

EXAMPLE 10

Unsaturated ester 11

A solution of the aldehyde 10 and 700 mg of methyl(-triphenylphosphoranylidene)acetate in 10 ml of THF was stirred 2 hours at RT. The solution was then concentrated under vacuum and the residue was partitioned between 40 ml of 5 hexanes: 1 EtOAc and 5 ml water/10 ml of saturated aqueous sodium bicarbonate solution. The organic phase was dried with sodium sulfate and the solvent removed under vacuum. Chromatography of the residue over silica gel (5 hexanes: 1 EtOAc) provided the title compound.

p.m.r.: (CDCl$_3$) δ1.04 (dd,3H), 1.38 (m,1H), 1.80 (m,1H), 2.02 (m,1H), 3.00 (m,1H), 3.30-3.45 (m,2H), 3.38 (s,3H), 3.68-3.80 (m,1H), 3.73 (dd,1H), 3.79 (s,3H), 4.51 (s,2H), 6.02-6.12 (dd,1H), 6.82-6.92 (dd,1H), 7.26-7.45 ppm (m,5H).

EXAMPLE 11

Methyl ester epoxide 12

A mixture of 3 g of the unsaturated ester 11 and 400 mg of 10% palladium on carbon in 120 ml of EtOAc was shaken in an atmosphere of hydrogen gas for 1.5 hour. The mixture was the filtered thru Celite and the filtrate concentrated under vacuum to provide the title compound.

EXAMPLE 12

Lactone 13

A mixture of the methyl ester epoxide 12 and 20 ml of 5N aqueous sodium hydroxide solution in 100 ml of ethanol was stirred at 100° C. for 3 days. The mixture was then concentrated under vacuum and 50 ml of brine was added and that mixture was extracted 3 times with 100 ml of EtOAc. The organic phase was dried with magnesium sulfate and concentrated under vacuum. The residue was dissolved in 50 ml of methylene chloride and 50 mg of camphor sulfonic acid was added. The solution was stirred at RT for 2 hours and 0.5 ml of triethylamine was added. The solution was concentrated and chromatography of the residue over silica gel (2 hexanes: 1 EtOAc) provided the title compound.

$[\alpha]_D^{23} = +3.8$ c=2.0 CHCl$_3$ p.m.r.: (CDCl$_3$) δ0.97 (d,3H), 1.64 (m,1H), 1.83 (m,2H), 2.12 (m,1H), 2.25 (m,1H), 2.53 (ddd,1H), 2.75 (ddd,1H), 3.36 (dd,1H), 3.39 (s,3H), 3.47 (dd,1H), 3.65 (d,1H), 3.39 (m,1H), 4.00 (dd,1H), 4.10 (m,1H) 4.52 (s,2H), 7.29-7.37 ppm (m,5H).

EXAMPLE 13

Dimethoxy lactone 14

A solution of 22 mg of the lactone 13 in 2 ml of methylene chloride was added to a solution of ca. 300 mg of diazomethane in methylene chloride. A solution of 0.200 ml of boron trifluoride etherate in 8 ml of methylene chloride was then added immediately. The solution was stirred for 5 minutes, then 0.100 ml of triethylamine was added and the mixture filtered thru silica gel. The filtrate was concentrated and chromatography of the residue over silica gel (3 hexanes: 2 EtOAc) provided the title compound.

$[\alpha]_D^{23} = +9.6$ c=2.0 CHCl$_3$ p.m.r.: (CDCl$_3$) δ1.02 (d,3H), 1.34-1.48 (m,1H), 1.75-1.95 (m,2H), 2.10 (m,1H), 2.24-2.36 (m,1H), 2.46-2.72 (m,2H), 3.31 (dd,1H), 3.37 (s,3H), 3.42 (s,3H), 3.47 (dd,1H), 3.68 (td,1H), 3.80 (m,1H), 3.95 (dd,1H), 4.49 (d,1H) 4.54 (d,1H), 7.29-7.38 ppm (m,5H).

EXAMPLE 14

Oxazolidone ether 16

To a solution of 3.21 g of the oxazolidone 15 in 40 ml of methylene chloride at $-78°$ C. was added 13.64 ml of a 1M dibutylboron triflate in methylene chloride solution and 2.6 ml of triethylamine. The reaction solution was stirred at 0° C. for 30 minutes, then it was cooled to −78° C. 3-(4-Methoxybenzyloxy)propanaldehyde (2.4 g) in 4 ml of methylene chloride was added and the reaction solution was stirred 30 minutes at −78° C. and then at RT for 1.5 hour. At the end of this time 100 ml of pH7 phosphate buffer was added, followed by addition of 30% aqueous hydrogen peroxide to the mixture at 0° C. The mixture was then extracted twice with diethyl ether and the aqueous phases were dried with sodium sulfate. The solution was concentrated under vacuum and chromatography of the residue over silica gel (2 hexanes: 1 EtOAc) provided the title compound.

p.m.r.: (CDCl$_3$) δ0.86 (d,3H), 1.75–1.95 (m,2H), 2.43–2.66 (m,2H), 3.33 (d,1H), 3.60–3.76 (m,2H), 3.82 (s,3H), 4.08–4.25 (m,2H), 4.46 (s,2H), 4.79 (m,1H), 5.00 (dd,1H), 5.05 (dd,1H), 5.62 (d,1H), 5.77–5.94 (m,1H), 6.84–6.93 (m,2H) 7.22–7.47 ppm (m,7H).

EXAMPLE 15

Oxazolidone benzylidine acetal 17

To a solution of 453 mg of the oxazolidone ether 16 in 15 ml of methylene chloride was added 500 mg of 2,3-dichloro-5,6-dicyano-1,4-benzoquinone and the reaction stirred at RT for 30 minutes. The reaction mixture was filtered thru silica gel and the filter washed with methylene chloride. The combined filtrates were washed with 50 ml of saturated aqueous sodium bicarbonate and then dried over sodium sulfate. Concentration of the solution under vacuum provided the title compound.

p.m.r.: (CDCl$_3$) δ0.85 (d,3H), 1.91 (dd,1H), 2.00 (dd,1H), 2.58 (m,2H), 2.98 (m,2H), 3.77 (s,3H), 3.95 (m,1H), 4.16 (m,1H), 4.27 (dd,1H), 4.45 (m,1H), 4.77 (m,1H), 6.84–6.90 (m,2H) 7.2–7.48 ppm (m,7H).

EXAMPLE 16

Benzylidine acetal acid 18

To a solution of 4.5 g of the oxazolidone 17 in 150 ml of THF and 50 ml of water was added 830 mg of lithium hydroxide and 9 ml of 30% hydrogen peroxide. The reaction was stirred at 0° C. for 1 hour then 80 ml of 1.5N aqueous sodium sulfite was added, followed by 30 ml of saturated sodium bicarbonate. The mixture was concentrated under vacuum until all the THF had been removed and the aqueous mixture was washed with methylene chloride. The aqueous solution was acidified with 2N aqueous hydrochloric acid to pH6 and the mixture extracted twice with EtOAc. The organic phases were dried with sodium and concentrated under vacuum to provide the title compound.

EXAMPLE 17

Benzylidine acetal alcohol 19

A solution of the acid 18 and 1 g of lithium aluminum hydride in 100 ml of ethyl ether was stirred at −20° C. for 30 minutes. EtOAc was added to the mixture to quench any unreacted LAH and 150 ml of a saturated aqueous potassium/sodium tartrate solution was added. The mixture was stirred at RT for 1 hour, then the ether layer was separated. The aqueous phase was extracted 2 times with EtOAc and the combined organic phases were dried over sodium sulfate. The solution was concentrated under vacuum and chromatography of the residue over silica gel (2 hexanes: 1 EtOAc) provided the title compound.

p.m.r.: (CDCl$_3$) δ1.93–2.36 (m,5H), 3.70 (m,1H), 3.81 (s,3H), 3.80 (m,1H), 3.96 (td,1H), 4.08 (m,1H), 4.31 (dd,1H), 5.04–5.15 (m,2H), 5.47 (s,1H), 5.76–5.92 (m,1H), 6.89 (d,2H), 7.40 ppm (d,2H).

EXAMPLE 18

Benzylidine acetal aldehyde 20

To a solution of 0.450 ml of oxalyl chloride in 15 ml of methylene chloride at −78° C. was added 0.9 ml of dimethylsulfoxide and the reaction solution stirred for 10 minutes. A solution of 540 mg of the alcohol 19 in 5 ml of methylene chloride was added followed by 3 ml of triethylamine. After 10 minutes, 25 ml of water was added and the mixture extracted with 30 ml of 1:1 hexanes: EtOAc. The organic phase was washed with brine and dried over sodium sulfate. Concentration under vacuum provided the title compound.

EXAMPLE 19

Unsaturated ester 21

A solution of 510 mg of the aldehyde 20 and 1.7 g of (carbethoxyethylidine)triphenylphosphorane in 10 ml of methylene chloride was refluxed overnight. Water (20 ml) was added and the mixture extracted with 1:1 hexanes:ethyl acetate. The organic phase was dried over magnesium sulfate and concentrated under vacuum to provide the title compound.

p.m.r.: (CDCl$_3$) δ1.32 (t,3H), 1.70 (dd,1H), 1.81 (dd,1H), 1.88 (d,3H), 2.20 (m,1H), 2.55–2.68 (m,1H), 2.70–2.84 (m,1H), 3.77 (m,1H), 3.83 (s,3H), 3.91 (td,1H), 4.17–4.30 (m,3H), 6.55 (dd,1H), 6.92 (d,2H), 7.44 ppm (d,2H).

EXAMPLE 20

Benzylidine acetal alcohol 22

A mixture of 720 mg of the ester 21 and 106 mg of LAH in 20 ml of diethyl ether was stirred at −20° C. for 1 hour, then ethyl acetate was added followed by a saturated aqueous potassium/sodium tartrate solution. The mixture was stirred for 2 hours and the phases separated. The aqueous phase was extracted with EtOAc and the combined organic phases were dried with sodium sulfate. The organic solution was concentrated under vacuum and chromatography of the residue over silica gel (3 hexanes: 2 ethyl acetate) provided the title compound.

EXAMPLE 21

Benzylidine acetal iodide 23

A solution of 520 mg of the alcohol 22, 50 mg of imidazole, 525 mg of triphenylphosphine and 663 mg of carbon tetrabromide in 10 ml of methylene chloride was stirred at 0° C. for 20 minutes. Brine (20 ml) was added and the mixture extracted with 40 ml of 4:1 hexanes:ethyl acetate. The organic phase was dried over sodium sulfate and concentrated under vacuum. The residue was dissolved in 30 ml of acetone and 1 g of sodium iodide was added. The mixture was refluxed for 10 minutes, then concentrated under vacuum. Water (30 ml) was added and the mixture was extracted with 10:1 hexanes:ethyl acetate. The organic phase was dried over sodium sulfate and concentrated under vacuum. Chromatography of the residue over silica gel (15 hexanes: 1 ethyl acetate) provided the title compound.

p.m.r.: (CDCl$_3$) δ1.44–1.55 (m,1H), 1.63–1.82 (m,1H), 1.83 (s,3H), 2.02–2.17 (m,1H), 2.50–2.63 (m,2H), 3.58–3.68 (m,1H), 3.82 (s,3H), 3.84–4.01 (m,3H), 4.26

(dd,1H), 4.96-5.08 (m,2H), 5.46 (s,1H), 5.47 (d,1H), 5.65-5.82 (m,1H), 6.81 (d,2H), 7.44 ppm (d,2H).

EXAMPLE 22

Benzylidine acetal lactone 24

To a solution of 50 mg of the dimethoxy lactone 14 in 0.4 ml of THF at −78° C. was added 0.35 ml of a 0.5M sodium bis(trimethylsilyl)amide in THF solution and the solution stirred for 30 minutes at −78° C. The iodide 23 (70 mg) was added and the solution was stirred for 30 minutes at −78° C. At the end of this time the reaction was quenched by the addition of 5 ml of a saturated aqueous ammonium chloride solution and the mixture was extracted with 2:1 hexanes: EtOAc. The organic phase was dried with sodium sulfate and concentrated under vacuum. Chromatography of the residue over silica gel (3 hexanes: 1 EtOAc) provided the title compound in a 8:1 ratio with a minor impurity. The title compound was further purified by HPLC.

p.m.r.: (CDCl$_3$) δ1.05 (m,3H), 1.32–1.55 (m,3H), 1.65 (m,3H), 1.63–1.95 (m,2H), 2.03–2.32 (m,4H), 2.43–2.56 (m,1H), 2.62–2.85 (m,3H), 3.25 (s,3H), 3.32 (m,1H), 3.42 (s,3H), 3.48 (dd,1H), 3.60–3.98 (m,5H), 3.82 (s,3H), 4.26 (dd,1H), 4.50 (d,1H), 4.56 (d,1H), 4.95–5.06 (m,3H), 5.47 (s,1H), 5.67–5.85 (m,1H), 6.89 (m,2H), 7.24–7.44 ppm (m,7H).

EXAMPLE 23

Diol 25

A solution of 70 mg of the benzylidine acetal lactone 24 in 2 ml of THF was added to a mixture of 150 mg of LAH in THF at −50° C. The mixture was stirred at 0° C. for 30 minutes. At the end of this time EtOAc was added followed by a saturated aqueous potassium/sodium tartrate solution. The mixture was extracted 3 times with EtOAc and the combined organic phases were dried with sodium sulfate, filtered and concentrated under vacuum. Chromatography of the residue over silica gel (3 EtOAc: 2 hexanes) provided the title compound.

$[\alpha]_D^{23} = +6.4$ c=1 CHCl$_3$ p.m.r.: (CDCl$_3$) δ1.01 (d,3H), 1.64 (s,3H), 1.36–2.13 (m,10H), 2.35 (m,1H), 2.56–2.68 (m,3H), 3.23–3.63 (m,8H), 3.35 (s,3H), 3.47 (s,3H), 3.81 (s,3H), 3.90 (td,1H), 4.24 (dd,1H), 4.52 (s,2H), 4.89–5.06 (m,3H), 5.45 (s,1H), 5.67–5.84 (m,1H), 6.89 (d,2H), 7.30–7.45 ppm (m,7H).

EXAMPLE 24

Primary tosylate 26

A mixture of 48 mg of the diol 25, 0.400 ml of triethylamine, 82 mg of p-toluenesulfonyl chloride and 1 mg of DMAP was stirred for 20 hours at RT. Water (0.3 ml) was added and the mixture was stirred for 30 minutes at RT. A saturated aqueous sodium bicarbonate solution (10 ml) was added and the mixture was extracted with 2:1 hexanes: EtOAc. The organic phase was dried over sodium sulfate, filtered and concentrated under vacuum. Chromatography of the residue over silica gel (3 hexanes: 1 EtOAc) provided the title compound.

$[\alpha]_D^{23} = +4.1$ c=1 CHCl$_3$

EXAMPLE 25

Siloxy tosylate 27

A mixture of 140 mg of the primary tosylate 26, 0.10 ml of 2,6-lutidine and 0.10 ml of t-butyldimethylsilyl triflate in 8 ml of methylene chloride was stirred at 0° C. for 1 hour. A few drops of water were added and the mixture concentrated under vacuum. The residue was diluted with diethyl ether and the solution filtered thru silica gel. The filtrate was concentrated under vacuum and chromatography of the residue over silica gel (6 hexanes: 1 EtOAc) provided the title compound.

$[\alpha]_D^{23} = +12.3$ c=2.0 CHCl$_3$

EXAMPLE 26

Intermediate 28

A mixture of 120 mg of the siloxy tosylate 27 and 2 ml of a 1.0M lithium triethylborohydride in THF solution in THF was stirred at RT for 2 hours. The mixture was cooled to 0° C. and water was carefully added, followed by 5 ml of a saturated aqueous sodium bicarbonate solution and 0.5 ml of 36% aqueous hydrogen peroxide solution. This mixture was stirred for 10 minutes, then 4 ml of 1.5M aqueous sodium bisulfite solution was added and the mixture extracted 2 times with 15 ml of 1:1 hexanes: EtOAc. The combined organic phases were dried with sodium sulfate and concentrated under vacuum. Chromatography of the residue over silica gel (7 hexanes: 1 EtOAc) provided the title compound.

$[\alpha]_D^{23} = +18.4$ c=1.0 CHCl$_3$ p.m.r.: (CDCl$_3$) δ0.10 (s,6H), 0.80 (d,3H), 0.93 (s,8H), 1.02 (d,3H), 3.25–3.33 (m,2H), 3.31 (s,3H), 3.40 (dd,1H), 3.45 (s,3H), 3.57 (td,1H), 3.82 (s,3H), 3.82–3.93 (m,1H), 4.24 (dd,1H), 4.83 (d,1H), 4.52 (s,2H), 4.96 (d,1H), 5.02 (d,1H), 5.46 (s,1H), 5.68–5.85 (m,1H), 6.91 (d,2H), 7.24–7.37 (m,5H), 7.43 ppm (d,2H).

What is claimed is:

1. A compound of the formula:

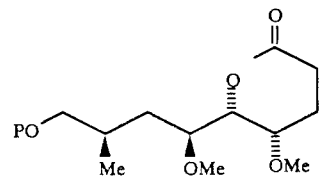

XIII where P is a hydroxy protecting group selected from: trisubstituted silyl, benzyl and protected benzyl, and aroyl and alkanoyl.

2. A compound of claim 1 of the structure:

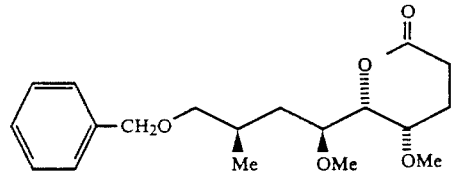

3. A compound of the formula:

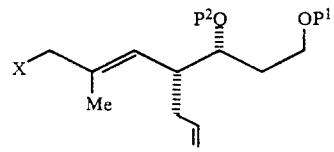

XXII where X is a halide and P1 and P2 are hydroxy protecting groups independently selected from: trisubstituted silyl, benzyl and protected benzyl, and aroyl and alkanoyl; or P1 and P2 may be combined to form an aromatic methine diradical.

4. A compound of claim 3 of the structure:

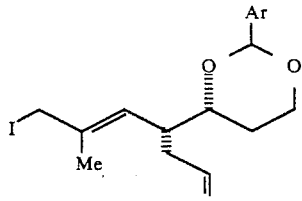

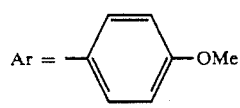

5. A compound of the formula:

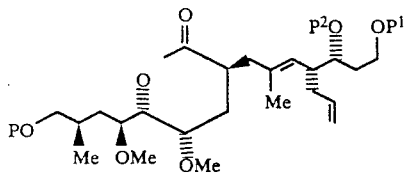 XXIII where P, P1 and P2 are hydroxy protecting groups independently selected from: trisubstituted silyl, benzyl and protected benzyl, and aroyl and alkanoyl; or P1 and P2 may be combined to form an aromatic methine diradical.

6. A compound of claim 5 of the structure:

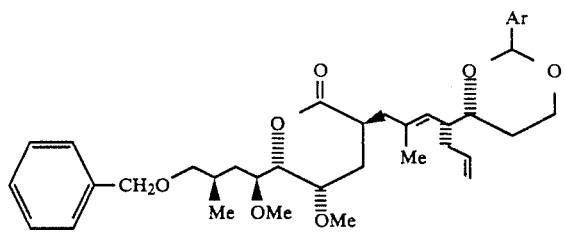

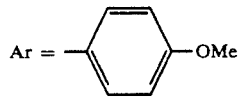

7. A compound of the formula:

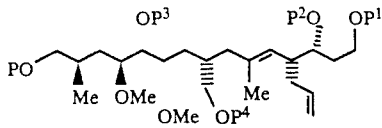 XXVI where P, P1, P2, P3 and P4 are independently hydrogen or hydroxy protecting groups independently selected from: trisubstituted silyl, benzyl and protected benzyl, and aroyl and alkanoyl; with the proviso that P3 and P4 are different, or P1 and P2 may be combined to form an aromatic methine diradical.

8. A compound of claim 7 of the structure:

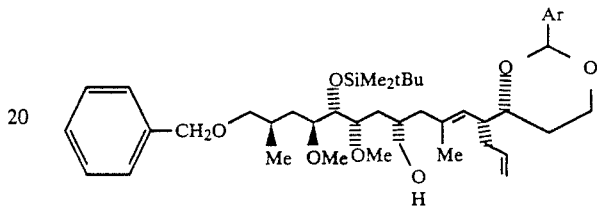

9. A compound of the formula:

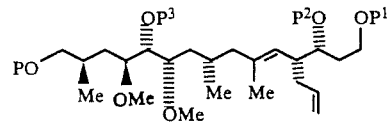 XXVII where P, P1, P2 and P3 are independently hydrogen or hydroxy protecting groups independently selected from: trisubstituted silyl, benzyl and protected benzyl, and aroyl and alkanoyl; or P1 and P2 may be combined to form an aromatic methine diradical.

10. A compound of claim 9 of the structure:

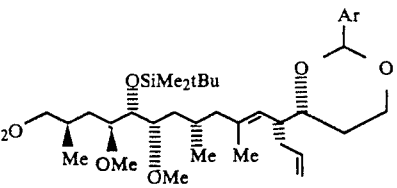

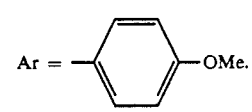

* * * * *